United States Patent [19]

Barer et al.

[11] 4,015,008

[45] Mar. 29, 1977

[54] N,N-DICHLORO SUBSTITUTED AMINOCARBOXYLIC ACIDS AS MICROBIOCIDES

[75] Inventors: Sol Joseph Barer, Elizabeth; Richard Frederick Stockel, Bridgewater Township; Peter Carl Valenti, East Windsor, all of N.J.

[73] Assignee: National Patent Development Corporation, New York, N.Y.

[22] Filed: Sept. 10, 1975

[21] Appl. No.: 611,972

Related U.S. Application Data

[62] Division of Ser. No. 438,712, Feb. 1, 1974, Pat. No. 3,950,536.

[52] U.S. Cl. .............................. 424/274; 424/244; 424/267

[51] Int. Cl.$^2$ .......................................... A01N 9/22
[58] Field of Search ............. 260/326.45; 424/274, 424/267, 244

[56] References Cited
FOREIGN PATENTS OR APPLICATIONS

2,102,173   8/1972   Germany .......................... 424/274

*Primary Examiner*—Frederick E. Waddell
*Attorney, Agent, or Firm*—Cushman, Darby & Cushman

[57] ABSTRACT

N-chloro nitrogen-containing carboxylic acids have been found to be useful as microbiocides in topical treatment of the skin and mucous membranes.

12 Claims, No Drawings

N,N-DICHLORO SUBSTITUTED AMINOCARBOXYLIC ACIDS AS MICROBIOCIDES

This is a division of application Ser. No. 438,712 filed Feb. 1, 1974, now U.S. Pat. No. 3,950,536.

The present invention relates to a novel microbiocidal composition and to the treatment of skin and mucous membranes with a microbiocide.

It has been found according to the invention that microbe infections of the skin or mucous membrane, e.g., infections caused by bacteria or fungi, can be effectively treated by applying a microbiocidally effective amount of an N-chloro nitrogen-containing carboxylic acid (hereinafter termed N-chlorocarboxylic compound for brevity) of the formulae:

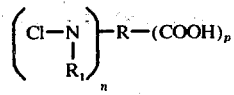

and

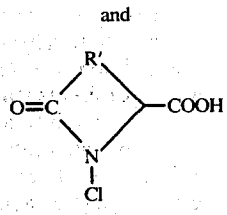

wherein R is a divalent saturated aliphatic hydrocarbon; $R_1$ is a monovalent saturated aliphatic hydrocarbon, acyl, or chlorine; $n$ is 1 or 2; $p$ is 1 or 2; R' is a divalent saturated aliphatic hydrocarbon having from 2 to 4 carbon atoms to complete the heterocyclic ring. In preferred embodiments of the invention, R is a divalent saturated aliphatic hydrocarbon (e.g., alkylene or alkylidene) of 1 to 17 carbon atoms; $R_1$ is alkyl of 1 to 4 carbon atoms; alkanoyl of 2-6 carbon atoms; or chlorine; and R' is ethylene ($CH_2CH_2$), trimethylene ($CH_2CH_2CH_2$), or tetramethylene ($CH_2CH_2CH_2CH_2$). Preferred subclasses of N-chlorocarboxylic compounds include, for example, N-chloroaminoalkanoic acid having 2 to 11 carbon atoms and $C_2$-$C_5$alkane bis(N-chloroamino) $C_2$-$C_5$alkanedioic acid. Preferred compounds include, by was of illustration, N,N-dichloro-beta-alanine, N,N-dichloro-11-aminoundecanoic acid, N-chloro-2-pyrrolidone-5-carboxylic acid, and N-chloro-N-acetyl-beta-alanine.

The compounds can be applied as such, in admixture with water, in admixture with triacetin, in admixture with water and triacetin, in creams, ointments or together with other conventional pharmaceutical adjuvants.

The compounds can also be applied conveniently in compositions of the type set forth in Evans U.S. Pat. No. 2,618,584, the entire disclosure of the Evans patent being hereby incorporated by reference. Thus, there can be used from 0.1, and lower, to 5, and higher weight per cent of the N-chlorinated compound with 99.9, and higher, to 95, and lower, weight percent of a citrate ester of the formula:

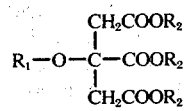

wherein $R_1$ is a monobasic acyl group of up to 12 carbon atoms and $R_2$ is alkyl of up to 12 carbon atoms, e.g., acetyl triethyl citrate. There can also be used esters of glycolic acid, malic acid and tartaric acid, e.g., diacetyl diethyl tartrate, acetyl ethyl malate, acetyl ethyl glycolate. There can also be used mixtures of these esters with triacetin, e.g., 1 to 99% by weight of either component as solvents for the N-chloroaminocarboxylic acid.

In general, microbiocidal activity has been observed by using concentrations as low as 0.1 weight percent, and lower, of the N-chlorocarboxylic compound, based on the weight of the resulting admixture. Practical considerations such as economics, skin sensitivity, etc., dictate an upper concentration limit of 5 weight percent, and sometimes slightly higher. A concentration range of from about 0.2 to about 3.0 weight percent is desirable for most cases.

The N-chloro carboxylic compounds can be formed in conventional fashion by reacting a positive halogen source such as a hypochlorite, e.g., t-butyl hypochlorite, isopropyl hypochlorite, ethyl hyopochlorite, calcium hypochlorite, lithium hypochlorite, sodium hypochlorite, hypochlorous acid, etc.; an N-chloromide, e.g., N-chlorosuccinimide, trichloroisocyanuric acid, etc.; or chlorine gas; with an aminocarboxylic acid or derivative such as glycine, sarcosine, alpha-aminoisobutyric acid, 4-aminobutyric acid, alanine, β-alanine, phenylalanine, norvaline, leucine, isoleucine, 11-amino-undecanoic acid, glutamic acid, valine, glutamine, lysine, alpha-aminobutyric acid, gamma-aminobutyric acid, alpha, epsilon-diaminopimelic acid, ethylene diaminodiacetic acid, 2-pyrrolidone-5-carboxylic acid, N-acetylbeta-alanine, N-caproyl-beta alanine, N-propionyl-beta alanine, N-acetyl glycine, 11-acetamido undecanoic acid, 18-aminostearic acid, 18-acetamidostearic acid, N-acetyl phenylalanine, N-ethyl alanine, N-ethyl glycine, 4-aminovaleric acid, caprolactam-7-carboxylic acid and valerolactam-6-carboxylic acid.

Examples of the N-chloro carboxylic compounds include N,N-dichloroglycine, N-chlorosarcosine, N,N-dichloroalpha-aminoisobutyric acid, N,N-dichloro-4-amino-butyric acid, N,N-dichloro-DL-alanine, N,N-dichloro-beta-alanine, N,N-dichlorophenylalanine, N,N-dichloronorvaline, N,N-dichloroleucine, N,N-dichloroisoleucine, N,N-dichloro-11-aminoundecanoic acid, N,N-dichloroglutamic acid, N,N-dichlorovaline, N,N-dichloroglutamine, N,N-dichlorotryptophan; N,N-dichlorolysine, N,N-dichloro-alpha-aminobutyric acid, N,N-dichloro-gamma-aminobutyric acid, N,N,N',N'-tetrachloro-alpha,epsilon-diaminopimelic acid, N,N'-dichloro-ethylenediaminodiacetic acid, N-chloro-2-pyrrolidone-5-carboxylic acid, N-chloro-N-acetyl-beta-alanine, N-chloro-N-caproyl-beta alanine, N-chloro-N-propionyl beta alanine, N-chloro-N-acetyl glycine, N-chloro-N-butyryl glycine, N-chloro-11-acetylaminoundecanoic acid, N,N-dichloro-18-aminostearic acid, N-chloro-18-acetylaminostearic acid, N-chloro-N-acetyl phenylalanine, N-chloro-N-ethyl alanine, N-chloro-N-ethyl glycine, N,N-dichloro-4-aminovaleric acid, N-chlorocaprolactam-7-carboxylic acid (2-homopiperidone-7-carboxylic acid) and N-chlorovalerolactam-6-carboxylic acid (2-piperidone-6-carboxylic acid). The preferred compounds are composed of C, H, O and N in addition to the N-chlorine atoms.

Typical examples of preparing the N-chloroaminocarboxylic acids are set forth below.

EXAMPLE 1

7.5 g of glycine is added to 75 ml of methanol and the mixture cooled to below 0° C. 26 ml of t-BuOCl is added dropwise, maintaining the temperature below 0° C. The reaction is followed by the gradual disappearance of the solid insoluble glycine to form a homogeneous solution of N,N-dichloroglycine.

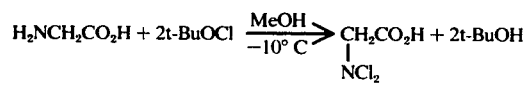

The methanol and the resulting t-butanol are stripped off under vacuum and the product obtained as a yellow-white powder with a strong chlorine odor. The yield is 98% and the purity, as determined by titration with $Na_2S_2O_3$ after treatment with KI, is 97%.

EXAMPLE 2

8.7 g Sarcosine is dissolved in 50 ml water and 150 ml of 5% sodium hypochlorite solution at 5° C. The reaction medium is acidified by HCl to pH=1 at low temperature, and 350 ml diethyl ether is added. The organic solvent is separated, dried with $Na_2SO_4$ stripped off under vacuum. The N-chlorosarcosine is obtained as a white powder in 80% yield and 90% purity.

The extraction of the N-chloro carboxylic compound from the aqueous solution may be aided by the addition of NaCl to aid in salting out the N-Cl derivative. A variety of organic solvents can be used to extract the compounds, including diethylether, chloroform, methylene chloride, carbon tetrachloride and a mixture of these solvents.

EXAMPLE 3

19 g of β-alanine is added to 150 ml methanol. The suspension is stirred and cooled to −25° C. 26 ml of t-BuOCl is added dropwise while maintaining the temperature at −∞ to 30° C. The gradual disappearance of most of the insoluble starting material indicates the progression of the reaction. The reaction is permitted to warm to room temperature with constant agitation and the insoluble β-alanine filtered. The methanol solution of N,N-dichloro-β-alanine is stripped of solvent to yield a green viscous liquid product in 94% yield and 91% purity.

EXAMPLE 4

5g of L-2-pyrrolidone-5-carboxylic acid is added to 30 ml methanol at 10° C. 4 ml of t-butyl hypochlorite is added dropwise while maintaining the temperature below 25° C. The resulting suspension is stirred for 0.5 hour whereupon there is formed a solution. The solution is stripped of solvent at room temperature, i.e., 22° C., under approximately 1 mm of Hg. There is obtained N-chloro-L-2-pyrrolidone-5-carboxylic acid in 95% purity and 100% yield.

Examples of other acid precursors reacted are given in Table A.

TABLE A

| REACTANT | PRODUCT | % YIELD |
|---|---|---|
| Valine $(CH_3)_2CHCHCO_2H$<br>$\|$<br>$NH_2$ | $(CH_3)_2CHCHCO_2H$<br>$\|$<br>$NCl_2$ | 80 |
| Leucine $(CH_3)_2CHCH_2CHCO_2H$<br>$\|$<br>$NH_2$ | $(CH_3)_2CHCH_2CHCO_2H$<br>$\|$<br>$NCl_2$ | 87 |
| Isoleucine $CH_3CH_2CH-CHCO_2H$<br>$\phantom{xxxxxxxxx}\|\phantom{xxx}\|$<br>$\phantom{xxxxxxxxx}CH_3\phantom{xx}NH_2$ | $CH_3CH-CH_2CHCO_2H$<br>$\|\phantom{xxxxx}\|$<br>$CH_3\phantom{xxx}NCl_2$ | 89 |
| 6-Aminocaproic acid<br>$H_2N(CH_2)_5CO_2H$ | $Cl_2N(CH_2)_5CO_2H$ | 90 |
| Glutamic acid<br>$HO_2C(CH_2)_2CHCO_2H$<br>$\|$<br>$NH_2$ | $HO_2C(CH_2)_2CHCO_2H$<br>$\|$<br>$NCl_2$ | 93 |
| 11-Aminoundecanoic acid<br>$H_2N(CH_2)_{10}CO_2H$ | $Cl_2N(CH_2)_{10}CO_2H$ | 94 |
| Ethylenediaminediacetic acid<br>$CH_2NHCH_2CO_2H$<br>$\|$<br>$CH_2NHCH_2CO_2H$ | $\phantom{xx}Cl$<br>$\phantom{xx}\|$<br>$CH_2NCH_2CO_2H$<br>$\|$<br>$CH_2-NCH_2CO_2H$<br>$\phantom{xxxxxx}\|$<br>$\phantom{xxxxxx}Cl$ | 94 |
| L-2-pyrrolidone-5-carboxylic acid | | |

TABLE A-continued

| REACTANT | PRODUCT | % YIELD |
|---|---|---|
| 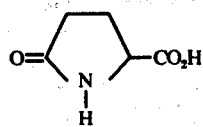 | 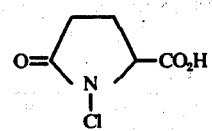 | 91 |

The compounds used in the present invention did not cause skin irritation in either animal or human tests. They are useful in treating microbe caused diseases of the skin and mucous membranes in mammals such as humans, mice, rats, cattle, dogs, sheep, cats, rabbits, horses, pigs, etc.

EXAMPLE 5

In the following Example, four Test Solutions were inoculated with viable cells, i.e., *Staphylococcus aureus*, saliva, *Escherichia coli*, *Streptococcus mutans*, *Canida albicans*, and *Aspergillus niger*. The four Test Solutions were as follows:

i. Solution of 1.0 weight percent of N,N-dichlorobeta-alanine in a mixture of water and triacetin. The volume of triacetin to water is 1:14.

ii. Solution of 0.5 weight percent of N,N-dichlorobeta-alanine in a mixture of water and triaetin. The volume of triacetin to water is 1:14.

iii. Solution of 0.1 weight percent of N,N-dichlorobeta-alanine in a mixture of water and triacetin. The volume of triacetin to water is 1:14.

iv. Solution of 0.01 weight percent of N,N-dichlorobeta-alanine in a mixture of water and triacetin. The volume of triacetin to water is 1:14.

The test organisms and inocula levels used in the experiments are identified below:

| Test Organisms | Viable Cells/Ml of Test Solution |
|---|---|
| Staphylococcus aureus | $10 \times 10^8$ |
| T. mentagrophytes | $75 \times 10^5$ |
| S. cerevisiae | $14 \times 10^7$ |
| S. faecalis | $9 \times 10^8$ |
| Canadian albicans | $40 \times 10^6$ |
| Aspergillus niger | $16 \times 10^6$ |

The test method employed was as follows: Nine milliliters of each test solution was inoculated under ambient conditions, e.g., about 22° C., with approximately one billion viable cells per milliliter. After 1, 5 and 10 minutes, one milliliter aliquots were transferred from the above said inoculated mixtures into 9 ml of neutralizing solution. The resulting solutions were subsequently serially diluted in 0.1 weight percent peptone water. Plates were poured with Tryptic Soy Agar for the bacteria and incubated at 37° C. for 48 hours. Yeast plates were poured with Mycophil Agar and incubated at 32° C. for 48-72 hours.

The neutralizing solution used to stop the bactericidal (or fungicidal) activity of the test organism is made by admixing 11.9 weight percent Tween 80, 1.7 weight percent Azolectin, 3 weight percent Tamol, and 1 weight percent peptone in water. The resulting mixture is boiled for about 15 minutes or until all components are dissolved. Thereafter, it is dispensed in desired volumes such as 9 ml, 99 ml, etc., and autoclaved at 250° F., 15 psig, for 15 minutes. Immediately upon removal from the sterilizer, i.e., while still very hot, the bottles should be well shaken since Tween tends to come out of solution during autoclaving. The function of this neutralizing solution is to render a bactericidal agent inactive by dispersing the molecules that give it its bactericidal properties. Upon cooling to room temperature, 0.1 grams sodium thiosulfate is added to each 9 milliliters of neutralizer. The function of the sodium thiosulfate is to reduce the active chlorine on the amino nitrogen atom of the chlorinated amino carboxylic acid.

Peptone is a nitrogen-containing nutrient by Difco Laboratories (Difco Manual of Dehydrated Culture Media and Reagents for Microbiological and Clinical Laboratory Procedure, Difco Laboratory Inc., 9th Edition, Detroit, Michigan, page 256 (1971)). Tween 80 is an emulsifier and solubilizer, polyoxyethylene 20 sorbitan monooleate sold by Atlas Chemical Company, Azolectin is lecithin sold by Associated Concentrates Company. Tamol is the sodium salt of condensed naphthalene sulfonic sold by Rohm and Haas Corporation.

The controls are described in further detail below. One milliliter of each Test Solution was placed in separate bottles containing 9 ml neutralizing solution and were well shaken. One and 0.1 ml aliquots of the resulting solutions were placed in sterile petri dishes. Each test organism was diluted to contain approximately 1,000 cells per ml. One-tenth ml. containing approximately 100 cells were placed directly on the above said 1 and 0.1 ml. aliquots. After 30 minutes, plates were poured with respective agars and incubated at appropriate temperatures. Organism controls consisted of placing 0.1 ml. of each cell suspension in a petri dish and poured with designated agars. After incubation, plates were counted to determine the number of organisms surviving the test solution plus exposure to neutralizing solution.

The number of viable organisms after exposure to varying concentrations N,N-dichloro-beta-alanine, i.e., the four Test Solutions, at the end of each time period (1 minute, 5 minutes, and 10 minutes) is set forth in Tables I through VI below.

Similar tests were carried out with other N-chloroaminocarboxylic acids within the invention with the results set forth below. The mixtures containing the N-chloroamino-carboxylic acids contained water and triacetin in the same ratio as was used with the N,N-dichloroneta-analine, i.e., 1 ml of triacetin and 14 ml of water plus sufficient of the N-chloroaminocarboxylic acid to give the indicated concentration. The effect on microorganisms of the mixture of water and triacetin alone is shown in Table X. It can be seen that this mixture by itself is ineffective as a microbiocide.

The percentages and parts unless otherwise indicated are by weight.

In primary skin irritation in albino rabbits, tests made with 0.05%, N,N-dichloro-beta-alanine-triacetin, 0.1%

N,N-dichloro-beta-alanine-triacetin, 0.5% N,N-dichloro-beta-alanine-triacetin, 1% N,N'-dichloro-beta-alanine-triacetin and 3% N,N-dichloro-beta-alanine-triacetin showed no primary skin irritation. No edema or erythema was observed after either 24 or 72 hours in either intact or abraded sites. The test method was essentially that of Draize et al "Methods for the Study of Irritation and Toxicity of Substances Applied Topically to the Skin and Mucous Membranes," *Journal Pharm. ɔ Exp. Ther.*,

TABLE I

| Test Solution | Activity After Test (Staphylococcus aureus $10 \times 10^8$) | | |
|---|---|---|---|
| | 1 Minute | 5 Minutes | 10 Minutes |
| 0.1 Wt. %-N,N-dichloro-β-alanine | < 100 | < 100 | < 100 |
| 0.01 Wt. %-N,N-dichloro-β-alanine | $17 \times 10^4$ | $57 \times 10^4$ | $39 \times 10^3$ |

TABLE II

| Test Solution | Activity After Test (C. albicans $40 \times 10^6$) | | |
|---|---|---|---|
| | 1 Minute | 5 Minutes | 10 Minutes |
| 0.1 Wt. %-N,N-dichloro-β-alanine | $15 \times 10^2$ | < 100 | < 100 |
| 0.01 Wt. %-N,N-dichloro-β-alanine | $12 \times 10^6$ | $33 \times 10^5$ | $18 \times 10^5$ |

TABLE III

| Test Solution | Activity After Test (T. mentagrophytes $75 \times 10^6$) | | |
|---|---|---|---|
| | 1 Minute | 5 Minutes | 10 Minutes |
| 1.0 Wt. %-N,N-dichloro-β-alanine | < 100 | < 100 | < 100 |
| 0.5 Wt. %-N,N-dichloro-β-alanine | < 100 | < 100 | < 100 |
| 0.1 Wt. %-N,N-dichloro-β-alanine | < 100 | < 100 | < 100 |

TABLE IV

| Test Solution | Activity After Test (A. niger $16 \times 10^6$) | | |
|---|---|---|---|
| | 1 Minute | 5 Minutes | 10 Minutes |
| 1.0 Wt. %-N,N-dichloro-β-alanine | < 100 | < 100 | < 100 |
| 0.5 Wt. %-N,N-dichloro-β-alanine | < 100 | < 100 | < 100 |
| 0.1 Wt. %-N,N-dichloro-β-alanine | $50 \times 100^4$ | < 100 | < 100 |

TABLE V

| Test Solution | Activity After Test (S. cerevisiae $14 \times 10^7$) | | |
|---|---|---|---|
| | 1 Minute | 5 Minutes | 10 Minutes |
| 1.0 Wt.%-N,N-dichloro-β-alanine | < 100 | < 100 | < 100 |
| 0.5 Wt.%-N,N-dichloro-β-alanine | < 100 | < 100 | < 100 |
| 0.1 Wt.%-N,N-dichloro-β-alanine | < 100 | < 100 | < 100 |

TABLE VI

| Test Solution | Activity After Test (S. faecalis $9 \times 10^8$) | | |
|---|---|---|---|
| | 1 Minute | 5 Minutes | 10 Minutes |
| 1.0 Wt.%-N,N-dichloro-β-alanine | < 100 | < 100 | < 100 |
| 0.5 Wt.%-N,N-dichloro-β-alanine | < 100 | < 100 | < 100 |
| 0.1 Wt.%-N,N-dichloro-β-alanine | < 100 | < 100 | < 100 |

TABLE VII

| Test Compound N,N-Dichloroglycine | Staphylococcus aureus $78 \times 10^8$ (gram +) - Test Organisms Number of Organisms Recovered After: | | |
|---|---|---|---|
| | 1 Minute | 5 Minutes | 10 Minutes |
| 20,000 ppm = 2.0 % | < 10 | < 10 | < 10 |
| 5,000 ppm = 0.5 % | < 10 | < 10 | < 10 |
| 1,000 ppm = 0.1 % | < 10 | < 10 | < 10 |

| Test Compound N,N-Dichloroglycine | Streptococcus faecalis $15 \times 10^9$ (gram +) - Test Organisms Number of Organisms Recovered After: | | |
|---|---|---|---|
| | 1 Minute | 5 Minutes | 10 Minutes |
| 20,000 ppm = 2.0 % | < 10 | < 10 | < 10 |
| 5,000 ppm = 0.5 % | < 10 | < 10 | < 10 |

TABLE VII-continued

| 1,000 ppm = 0.1 % | < 10 | < 10 | < 10 |
|---|---|---|---|

| Test Compound N,N-Dichloroglycine | Trycophyton mentagrophytes 65 × 10⁴ (fungus) - Test Organisms Number of Organisms Recovered After: | | |
|---|---|---|---|
| | 1 Minute | 5 Minutes | 10 Minutes |
| 20,000 ppm = 2.0 % | < 10 | < 10 | < 10 |
| 5,000 ppm = 0.5 % | < 10 | < 10 | < 10 |
| 1,000 ppm = 0.1 % | < 10 | < 10 | < 10 |

TABLE VIII

| Test Compound N,N-dichloroethylene-diamino diacetic acid | S. aureus 8 × 10⁶ - Test Organisms Number of Organisms Recovered After: | | |
|---|---|---|---|
| | 1 Minute | 5 Minutes | 10 Minutes |
| 20,000 ppm = 2.0 % | INSOLUBLE | | |
| 2,000 ppm = 0.2 % | < 10 | < 10 | < 10 |
| 200 ppm = 0.02% | TNTC* | TNTC | TNTC |

| Test Compound N,N-dichloroethylene-diamino diacetic acid | P. vulgaris 25 × 10⁷ - Test Organisms Number of Organisms Recovered After: | | |
|---|---|---|---|
| | 1 Minute | 5 Minutes | 10 Minutes |
| 20,000 ppm = 2.0 % | INSOLUBLE | | |
| 2,000 ppm = 0.2 % | < 10 | < 10 | < 10 |
| 200 ppm = 0.02% | 37 × 10³ | 28 × 10³ | 10 |

| Test Compound N,N-dichloroethylene-diamino diacetic acid | C. albicans 49 × 10⁶ - Test Organisms Number of Organisms Recovered After: | | |
|---|---|---|---|
| | 1 Minute | 5 Minutes | 10 Minutes |
| 20,000 ppm = 2.0 % | INSOLUBLE | | |
| 2,000 ppm = 0.2 % | < 10 | < 10 | < 10 |
| 200 ppm = 0.20% | 94 × 10⁵ | 72 × 10⁵ | 91 × 10⁵ |

| Test Compound N,N-dichloroethylene-diamino diacetic acid | A. pullulans 22 × 10⁴ - Test Organisms Number of Organisms Recovered After: | | |
|---|---|---|---|
| | 1 Minute | 5 Minutes | 10 Minutes |
| 20,000 ppm = 2.0 % | INSOLUBLE | | |
| 2,000 ppm = 0.2% | < 10 | < 10 | < 10 |
| 200 ppm = 0.02% | 16 × 10² | 37 × 10² | 23 × 10² |

*TNTC = Too Numerous To Count

TABLE IX

| Test Compound N,N-Dichloroamino-undecanoic Acid | S. aureus 85 × 10⁸ - Test Organisms Number of Organisms Recovered After: | | |
|---|---|---|---|
| | 1 Minute | 5 Minutes | 10 Minutes |
| 20,000 ppm = 2.0 % | 410 | 30 | < 10 |
| 5,000 ppm = 0.5 % | 76 × 10³ | 13 × 10² | < 10 |
| 1,000 ppm = 0.1 % | 44 × 10⁵ | 320 | < 10 |

| Test Compound N,N-dichloroamino-undecanoic Acid | S. faecalis 16 × 10⁹ - Test Organisms Number of Organisms Recovered After: | | |
|---|---|---|---|
| | 1 Minute | 5 Minutes | 10 Minutes |
| 20,000 ppm = 2.0 % | < 10 | < 10 | < 10 |
| 5,000 ppm = 0.5 % | 480 | < 10 | < 10 |
| 1,000 ppm = 0.1 % | 89 × 10⁶ | 470 | < 10 |

| Test Compound N,N-dichloroamino-undecanoic Acid | T. mentagraphytes 64 × 10⁴ - Test Organisms Number of Organisms Recovered After: | | |
|---|---|---|---|
| | 1 Minute | 5 Minutes | 10 Minutes |
| 20,000 ppm = 2.0 % | 690 | < 10 | < 10 |
| 5,000 ppm = 0.5 % | 24 × 10³ | < 10 | < 10 |
| 1,000 ppm = 0.1 % | 35 × 10³ | < 10 | < 10 |

TABLE X

| Triacetin Control 1 ml + 14 ml H₂O | S. aureus - Organism and Inoculum Number of Organisms Recovered After: | | |
|---|---|---|---|
| | 1 Minute | 5 Minutes | 10 Minutes |
| | 94 × 10⁶ | 83 × 10⁶ | 93 × 10⁶ |

S. faecalis - Organism and Inoculum

TABLE X-continued

| Triacetin Control 1 ml + 14 ml H$_2$O | Number of Organisms Recovered After: | | |
|---|---|---|---|
| | 1 Minute | 5 Minutes | 10 Minutes |
| | 77 × 10$^6$ | 91 × 10$^6$ | 85 × 10$^6$ |

| Triacetin Control 1 ml + 14 ml H$_2$O | T. mentagraphytes - Organism and Inoculum Number of Organisms Recovered After: | | |
|---|---|---|---|
| | 1 Minute | 5 Minutes | 10 Minutes |
| | 42 × 10$^4$ | 46 × 10$^4$ | 48 × 10$^4$ |

TABLE XI

| Test Compound N,N-dichloro-4-amino butyric acid | S. aureus 10 × 10$^8$ - Test Organisms Number of Organisms Recovered After: | | |
|---|---|---|---|
| | 1 Minute | 5 Minutes | 10 Minutes |
| 20,000 ppm = 2.0 % | < 10 | < 10 | < 10 |
| 2,000 ppm = 0.2 % | < 10 | < 10 | < 10 |
| 200 ppm = 0.02% | 25 × 10$^3$ | 26 × 10$^2$ | < 10 |

| Test Compound N,N-dichloro-4-amino butyric acid | P. vulgaris 29 × 10$^7$ - Test Organisms Number of Organisms Recovered After: | | |
|---|---|---|---|
| | 1 Minute | 5 Minutes | 10 Minutes |
| 20,000 ppm = 2.0 % | < 10 | < 10 | < 10 |
| 2,000 ppm = 0.2 % | < 10 | < 10 | < 10 |
| 200 ppm = 0.02% | < 10 | < 10 | < 10 |

| Test Compound N,N-dichloro-4-amino butyric acid | Asp. niger 18 × 10$^6$ - Test Organisms Number of Organisms Recovered After: | | |
|---|---|---|---|
| | 1 Minute | 5 Minutes | 10 Minutes |
| 20,000 ppm = 2.0 % | < 10 | < 10 | < 10 |
| 2,000 ppm = 0.2 % | 2 = 10$^2$ | < 10 | < 10 |
| 200 ppm = 0.02% | 30 × 10$^4$ | 10 × 10$^4$ | 8 × 10 |

| Test Compound N,N-dichloro-4-amino butyric acid | C. albicans 26 × 10$^6$ - Test Organisms Number of Organisms Recovered After: | | |
|---|---|---|---|
| | 1 Minute | 5 Minutes | 10 Minutes |
| 20,000 ppm = 2.0 % | < 10 | < 10 | < 10 |
| 2,000 ppm = 0.2 % | < 10 | < 10 | < 10 |
| 200 ppm = 0.02% | 24 × 10$^4$ | 8 × 10$^3$ | 45 × 10 |

| Test Compound N,N-dichloroglycine | S. aureus - Test Organisms Number of Organisms Recovered After: | | |
|---|---|---|---|
| | 1 Minute | 5 Minutes | 10 Minutes |
| 1,000 ppm = 0.01% | < 10 | < 10 | < 10 |

| Test Compound N,N-dichloroglycine | P. vulgaris - Test Organism Number of Organisms Recovered After: | | |
|---|---|---|---|
| | 1 Minute | 5 Minutes | 10 Minutes |
| 1,000 ppm = 0.01% | < 10 | < 10 | < 10 |

| Test Compound N,N-dichloroglycine | A. niger - Test Organisms Number of Organisms Recovered After: | | |
|---|---|---|---|
| | 1 Minute | 5 Minutes | 10 Minutes |
| 1,000 ppm = 0.01% | 37 × 10$^4$ | 17 × 10$^3$ | < 50 |

| Test Compound N,N-dichloroglycine | C. albicans Number of Organisms Recovered After: | | |
|---|---|---|---|
| | 1 Minute | 5 Minutes | 10 Minutes |
| 1,000 ppm = 0.01% | 47 × 10$^4$ | < 10 | < 10 |

TABLE XII

| Test Compound L-N-Chloro-2-Pyrrolidone-5-carboxylic acid | S. aureus 12 × 10$^8$ - Test Organisms Number of Organisms Recovered After: | | |
|---|---|---|---|
| | 1 Minute | 5 Minutes | 10 Minutes |
| 5,000 ppm = 0.5 wt. % | 10 | 10 | 10 |
| 1,000 ppm = 0.1 wt. % | 180 | 10 | 10 |
| 500 ppm = 0.05 wt. % | 21 × 10$^4$ | 47 × 10$^3$ | 10 |

| Test Compound L-N-Chloro-2-Pyrrolidone-5-carboxylic acid | P. vulgaris - 14 × 10$^7$ - Test Organisms Number of Organisms Recovered after: | | |
|---|---|---|---|
| | 1 Minute | 5 Minutes | 10 Minutes |
| 5,000 ppm = 0.5 wt. % | 10 | 10 | 10 |
| 1,000 ppm = 0.1 wt. % | 10 | 10 | 10 |

TABLE XII-continued

| | T. Mentagraphytes 7 × 10⁵ - Test Organisms Number of Organisms Recovered After: | | |
|---|---|---|---|
| 500 ppm = 0.05 wt. % | 10 | 10 | 10 |
| Test Compound L-N-Chloro-2-pyrrolidone-5-Carboxylic Acid | 1 Minute | 5 Minutes | 10 Minutes |
| 5,000 ppm = 0.5 wt. % | 10 | 10 | 10 |
| 1,000 ppm = 0.1 wt. % | 10 | 10 | 10 |
| 500 ppm = 0.05 wt. % | 10 | 10 | 10 |

Vol. 82, page 377 (1944). At each dosage level there were used six albino New Zealand rabbits ranging in weight from 1.8 – 2.4 kg.

The method consisted of applying the test material (0.5 ml) to clipped areas of intact and abraded skin to the extent of approximately 10% of the total body surface of the animal. The abrasions were longitudinal epidermal incisions sufficiently deep to penetrate the stratum corneum, but not so deep as to destroy the integrity of the derma. Following application of the test material, the entire trunk of the animal was wrapped in an impervious sheeting. The animals were then immobilized. The sites were individually examined and rated separately for erythema and edema at 24 and 72 hours. The mean scores for 24 and 72 hour gradings were averaged to determine final irritation indices. As stated, no irritation was noted on a scale ranging from 0 to 4 for either erythema or edema.

No erythema is 0, very slight erythema is 1 (barely perceptible), on up to severe erythema (beet redness) to slight eschen formation (injuries in depth) is 4.

Similarly, no edema is 0, very slight edema (barely perceptible) is 1, on up to severe edema (raised more than 1 mm. and extending beyond area of exposure) is 4.

In in vivo human skin tests using 2%, 1% and 0.5% N,N-dichloro-beta-alanine-triacetin, untreated control, triacetin control and skin control the following procedure was used and the following results were obtained:

PROCEDURE

Occlusive patches were made with dermicil hypoallergenic tape and commercial Saran. Patches measured 2 × 2. One-tenth ml. of each test concentration was placed on an area of skin marked off at ¾ × ¾.

A patch was placed over each test area and remained there for 48 hours.

TEST SAMPLING

After 48 hours each treated area was sampled: 1.5 ml. of 9% Saline was introduced into a sterile sampling cup which had been placed well within the treated area of skin. The Saline was agitated with a sterile pipette for 30 seconds after which 1 ml. was withdrawn and placed in 9 ml. peptone water.

Tubes were serially diluted, plated out and poured with Brain Heart infurion agar.

RESULTS

| | Number of Microorganisms per cm² Recovered From Each Test Area After 48 Hours. |
|---|---|
| 2% | 0 |
| 1% | 0 |
| 0.5% | 0 |
| Untreated Control (Patch placed over untreated skin) | 25 × 10⁵ |
| Triacetin Control | 69 × 10³ |
| Skin Control - To determine no. of cells normally found on innoccluded skin | - 30 |
| No irritation whatsoever was observed. | |

The diseases caused by some of the organisms tested are:

| | |
|---|---|
| C. albicans: | 1) Thrush (infection of mucous membranes) |
| | 2) Cutaneous moniliasis: infection between fingers |
| | 3) Moniliasis of respiratory tract |
| S. aureus: | 1) Food Poisoning |
| | 2) Boils and Carbuncles |
| | 3) Precursors to majority of cases of osteomyelitis and periostitis, otitis media, sinusitis |
| | 4) In animals: a. mastitis b. staph infection of lambs |
| Strep. faecalis: | 1) Subacute bacterial endocardites |
| T. mentagrophytes: | 1) Commonest cause of athlete's foot |
| | 2) Ringworm of smooth skin |
| | 3) Folliculities of scalp and beard |
| | 4) Intertrigeneous infections |

As previously indicated the N-chloro carboxylic compounds employed in the present invention are preferably applied to skin or mucous membranes in water-triacetin solutions such as those used in the bactericidal and fungicidal tests set forth above. The proportions of materials are not critical. The N-chloro compound can be present in an amount up to its solubility. Conveniently they are used at a concentration of 0.01 to 1%. The preferred concentration will vary, of course, with each N-chloro compound and the particular skin or mucous membrane condition to be treated, i.e., the microorganism involved.

What is claimed is:

1. A method for treating fungal and bacterial infections of any area of the skin or mucous membrane comprising bringing said area into contact with a microbiocidally effective amount of an N-chloro carboxylic acid compound having the formula:

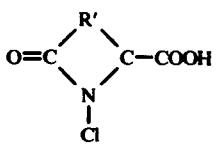

wherein R' is a divalent aliphatic hydrocarbon group having 2 to 4 carbon atoms.

2. A method according to claim 1 wherein the infection is caused by *S. aureus*, *P. vulgaris*, *T. mentagraphytes*, *C. albicans*, *Strep. faecalis*, *S. cerevisiae* or *Aspergillus niger*.

3. A method according to claim 2 wherein R' is ethylene, trimethylene or tetramethylene.

4. A method according to claim 3 wherein the N-chloro carboxylic acid compound is N-chloro-2-pyrrolidone-5-carboxylic acid.

5. A method according to claim 1 wherein $R^1$ is ethylene, trimethylene or tetramethylene.

6. A method according to claim 1 wherein the compound is N-chloro-2-pyrrolidone-5-carboxylic acid.

7. A method according to claim 6 wherein the N-chloro-carboxylic acid compound is applied to the skin.

8. A method according to claim 7 wherein the skin is in the area of the toes.

9. A method according to claim 7 wherein the skin is in the area of the fingers.

10. A method according to claim 7 wherein the skin is in the area of the scalp.

11. A method according to claim 7 wherein the skin is in the area of the face.

12. A method according to claim 7 wherein the N-chloro-carboxylic acid compound is N-chloro-2-pyrrolidone-5-carboxylic acid and the infection is caused by *S. aureus*, *P. vulgaris* or *T. mentagraphytes*.

* * * * *